(12) United States Patent
Gleba et al.

(10) Patent No.: US 7,667,091 B2
(45) Date of Patent: Feb. 23, 2010

(54) METHOD OF ENCODING INFORMATION IN NUCLEIC ACIDS OF A GENETICALLY ENGINEERED ORGANISM

(75) Inventors: Yuri Gleba, Halle/Saale (DE); Victor Klimyuk, Halle/Saale (DE)

(73) Assignee: Icon Genetics GmbH, Munich (DE)

( * ) Notice: Subject to any disclaimer, the term of this patent is extended or adjusted under 35 U.S.C. 154(b) by 538 days.

(21) Appl. No.: 10/471,960

(22) PCT Filed: Dec. 19, 2001

(86) PCT No.: PCT/EP01/15034

§ 371 (c)(1),
(2), (4) Date: Apr. 5, 2004

(87) PCT Pub. No.: WO02/079481

PCT Pub. Date: Oct. 10, 2002

(65) Prior Publication Data

US 2004/0191788 A1    Sep. 30, 2004

(30) Foreign Application Priority Data

Mar. 29, 2001   (DE) ................................ 101 15 507

(51) Int. Cl.
C12Q 1/68       (2006.01)
C12N 15/74      (2006.01)
C12N 15/00      (2006.01)
C12N 15/87      (2006.01)

(52) U.S. Cl. ............................. 800/21; 435/6; 435/471; 800/278

(58) Field of Classification Search ............... None
See application file for complete search history.

(56) References Cited

U.S. PATENT DOCUMENTS

| | | | |
|---|---|---|---|
| 5,139,812 A | 8/1992 | Lebacq |
| 5,474,925 A | 12/1995 | Maliyakal et al. |
| 5,576,198 A | 11/1996 | McBride et al. |
| 5,627,059 A | 5/1997 | Capecchi et al. |
| 5,670,623 A | 9/1997 | Shoseyov et al. |
| 5,723,765 A | 3/1998 | Oliver et al. |
| 5,877,402 A | 3/1999 | Maliga et al. |
| 6,100,448 A | 8/2000 | Thompson et al. |
| 6,147,278 A | 11/2000 | Rogers et al. |
| 6,174,700 B1 | 1/2001 | Haynes et al. |
| 6,300,545 B1 | 10/2001 | Baszczynski et al. |
| 6,331,416 B1 | 12/2001 | Shani et al. |
| 6,331,661 B1 | 12/2001 | Baszczynski et al. |
| 6,781,033 B2 | 8/2004 | Staub et al. |
| 2003/0188337 A1 | 10/2003 | Day et al. |
| 2004/0055037 A1 | 3/2004 | Gleba et al. |
| 2004/0083499 A1 | 4/2004 | Eibl et al. |
| 2004/0088764 A1 | 5/2004 | Gleba et al. |
| 2004/0137631 A1 | 7/2004 | Herz et al. |
| 2004/0191788 A1 | 9/2004 | Gleba et al. |
| 2004/0221330 A1 | 11/2004 | Klimyuck et al. |
| 2004/0244073 A1 | 12/2004 | Klimyuck et al. |
| 2004/0255347 A1 | 12/2004 | Klimyuck et al. |
| 2005/0014150 A1 | 1/2005 | Atabekov et al. |
| 2005/0015829 A1 | 1/2005 | Koop et al. |
| 2005/0015830 A1 | 1/2005 | Dorokhov et al. |
| 2005/0059004 A1 | 3/2005 | Atabekov et al. |
| 2005/0066384 A1 | 3/2005 | Klimyuck et al. |
| 2005/0091706 A1 | 4/2005 | Klimyuck et al. |

FOREIGN PATENT DOCUMENTS

| | | |
|---|---|---|
| EP | 0270 248 | 6/1988 |
| EP | 1 045 037 | 10/2000 |
| WO | 87/00551 | 1/1987 |
| WO | 94/16089 | 7/1994 |
| WO | 95/34668 | 12/1995 |
| WO | WO96/17954 | 6/1996 |
| WO | 98/09505 | 3/1998 |
| WO | 98/44097 | 10/1998 |
| WO | 98/54342 | 12/1998 |
| WO | 99/25821 | 5/1999 |
| WO | 99/25855 | 5/1999 |
| WO | 99/36516 | 7/1999 |
| WO | 01/11020 | 2/2000 |
| WO | 00/17365 | 3/2000 |
| WO | 00/20611 | 4/2000 |
| WO | 00/32799 | 6/2000 |

(Continued)

OTHER PUBLICATIONS

Wu, J. Bicteriol., 178(19):5817-5821 (1996).*

(Continued)

*Primary Examiner*—Shubo(Joe) Zhou
(74) *Attorney, Agent, or Firm*—Myers Bigel Sibley & Sajovec, P.A.

(57) ABSTRACT

The present invention provides a method of producing a genetically engineered transgenic organism, by (a) incorporating into the organism a functional DNA sequence that confers a trait on an organism and (b) incorporating into the organism a non-functional DNA sequence, wherein the non-functional DNA sequence encodes an information message using a predefined coding scheme, wherein the information message provides information about the functional DNA sequence, and the predefined coding scheme can be used to map a plurality of information messages into a plurality of non-functional DNA sequences and additionally, the functional and the non-functional DNA sequence are incorporated into the same chromosome of the organism.

25 Claims, 5 Drawing Sheets

FOREIGN PATENT DOCUMENTS

| | | |
|---|---|---|
| WO | 00/68391 | 11/2000 |
| WO | 00/68431 | 11/2000 |
| WO | 00/70019 | 11/2000 |
| WO | WO00/68431 | 11/2000 |
| WO | 00/77174 | 12/2000 |
| WO | 00/77175 | 12/2000 |
| WO | 00/78985 | 12/2000 |
| WO | 01/59138 | 8/2001 |
| WO | 01/81600 | 11/2001 |
| WO | 02/12522 | 2/2002 |
| WO | 02/29068 | 4/2002 |
| WO | 02/46438 | 6/2002 |
| WO | 02/46440 | 6/2002 |
| WO | 02/055651 | 7/2002 |
| WO | 02/057466 | 7/2002 |
| WO | 02/068664 | 9/2002 |
| WO | 02/077246 | 10/2002 |
| WO | 02/079481 | 10/2002 |
| WO | 02/088369 | 11/2002 |
| WO | 02/101060 | 12/2002 |
| WO | 03/001900 | 1/2003 |
| WO | 03/004658 | 1/2003 |
| WO | 03/020927 | 3/2003 |
| WO | 03/020928 | 3/2003 |
| WO | 03/020938 | 3/2003 |

OTHER PUBLICATIONS

Derbyshire, PNAS, 95:1356-1357 (1998).*
Santz et al. "Altered local and systemic spread of movement deficient virus in transgenic tobacco plants expressing the cucumber mosaic virus 3a protein" *Arch Virol.* 145:2387-2401 (2000).
Parry et al. "Construction of a bidirectional promoter probe vector and its use in analyzing *nod* gene expression in *Rhizobium loti*" Gene 150:105-109 (1994).
Hagemann et al. "Extranuclear Inheritance: Plastid Genetics" *Progress in Botany*, vol. 55, 260-275 (1994).
Klaus et al. "Generation of Marker Free Plastid Transformants Using a Transiently Cointegrated Selection Gene" *Nature Biotechnology* 22: 225-229 (2004).
Mühlbauer et al. "Functional analysis of plastid DNA replication origins in tobacco by targeted inactivation" *The Plant Journal*, 32:175-184 (2002).
Ruf et al. "Stable Genetic Transformation of Tomato Plastids and Expression of a Foreign Protein in Fruit" *Nature Biotechnology* 19: 870-875 (2001).
Shimada et al. "Fine Structural Features of the Chloroplast Genome: Comparison of the Sequenced Chloroplast Genomes" *Nucleic Acids Research* 19: 983-995(1991).
Shinozaki et al. "The Complete Nucleotide Sequence of the Tobacco Chloroplast Genome: Its Gene Organization and Expression" *The EMBO Journal* 5: 2043-2049 (1986).
Sidorov et al. "Stable Chloroplast Transformation in Potato: Use of Green Fluorescent Protein as a Plastid Marker" *The Plant Journal* 19: 209-216 (1999).
Albert et al. (1995) "Site-specific integration of DNA into wild-type and mutant lox sites placed in the plant genome" The Plant Journal 7:649-659.
Allison et al., "Deletion of rpoB Reveals a Second Distinct Transcription System in Plastids of Higher Plants," The EMBO Journal, 15:11 2802-2809 (1996).
Altschul et al. "Basic Local Alignment Search Tool," J. Mol. Biol., 215:403-410 (1990).
Anandalakshmi et al. (1998) "A viral suppressor of gene silencing in plants" Proc. Natl. Acad. Sci. U.S.A. 95:13079-13084.
Anandalakshmi et al. (2000) "A calmodulin-related protein that suppresses posttranscriptional gene silencing in plants" Science 290:142-144.
Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.
Bateman et al. (2000) "Tools for chloroplast transformation in Chlamydomonas: expression vectors and a new dominant selectable marker" Mol. Gen. Genet. 263:401-410.
Bergamini et al. "Picornavirus IRESes and the Poly(A) tail Jointly Promote Cap-Independent Translation in a Mammalian Cell-free System," RNA, 6:1781-1790 (2000).
Bogorad, Lawrence, "Engineering Chloroplasts: an Alternative Site for Foreign Genes, Proteins, Reactions and Products," TIBTECH, 18:257-263 (Jun. 2000).
Bouchez et al. (1993) "A binary vector based on Basta resistance for in planta transformation of *Arabidopsis thaliana*" C. R. Acad. Sci. Paris, Science de la vie 316:1188-1193.
Boynton et al., "Chloroplast Transformation in Chlamydomonas with High Velocity Microprojectiles," Science, 240:1534-1538 (1688).
Carpin et al. (2001) "Identification of a Ca2+-Pectate Binding Site on an Apoplastic Peroxidase" The Plant Cell 13:511-520.
Chappell et al. "A 9-nt Segment of Cellular mRNA Can Function as an Internal Ribosome Entry Site (IRES) and When Present In Linked Multiple Copies Greatly Enhances IRES Activity," PNAS, 97(4):1536-1541 (Feb. 15, 2000).
Coutts et al. "Development of Geminivirus-based Gene Vectors for Dicotyledonous Plants" Australian Journal of Plant Physiology 17:365-375(1990).
Dale et al. "Intra- and intermolecular site-specific recombination in plant cells mediated by bacteriophage P1 recombinase" Gene 91:79-85(1990).
Dale et al. "Mutations in the CRE/LOX Recombination Site Enhance the Stability of Recombination Products: Applications for Gene Targeting in Plants" Journal of Cellular Biochemistry 50 (S16S):206. (1992).
Daniell, "New Tools for Chloroplast Genetic Engineering," Nature Biotechnology, 17:855-856 (Sep. 1999).
De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).
Domingo et al. (1999) "Identification of a novel peptide motif that mediates cross-linking of proteins to cell walls" the Plant Journal 20:563-570.
Dorokhov et al. "Polypurine (A)-Rich Sequences Promote Cross-Kingdom Conservation of Internal Ribosome Entry" PNAS 99(8):5301-5306 (Apr. 16, 2002).
Drescher et al., "The Two Largest Chloroplast Genome-Encoded Open Reading Frames of Higher Plants are Essential Genes," The Plant Journal, 22(2):97-104 (2000).
El-Sheekh, M.M. (2000) "Stable Chloroplast Transformation in *Chlamydomonas reinhardtii* using Microprojectile Bombardment" Folia Microbiol. 45(6) 496-504.
Fischer et al., "Selectable Marker Recycling in the Chloroplast," Mol. Gen. Genet., 251:373-380 (1996).
Gatz et al. (1991) "Regulation of a modified CaMV 35S promoter by the Tn10-encoded Tet repressor in transgenic tobacco" Mol. Gen. Genet. 227:229-237.
Hager at al., "Enslaved Bacteria as New Hope for Plant Biotechnologists," Appl. Microbiol. Biotechnol., 54:302-310 (2000).
Heifetz, Peter B., "Genetic Engineering of the Chloroplast," Biochimie, 82:655-666 (2000).
Hoff et al. (2001) "A recombinase-mediated transcriptional induction system in transgenic plants" Plant Mol. Biol. 45:41-49.
Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).
Houdebine et al. "Internal Ribosome Entry Sites (IRESs): Reality and Use" Transgenic Research, 8:157-177 (1999).
Iamtham et al. (2000) "Removal of antibiotic resistance genes from transgenic tobacco plastids" 18:1172-1176.
Ivanov et al. "A Tobamovirus Genome That Contains an Internal Ribosome Entry Site Functional In Vitro," Virology, 232:32-43 (1997).

Jeon et al. (2000) "T-DNA insertional mutagenesis for functional genomics in rice" Plant J. 22:561-570.

Kofer et al., "PEG-Mediated Plastid Transformation in Higher Plants," In Vitro Cell. Dev. Biol.- Plant, 31:303-309 (1998).

Koshinsky et al. (2000) "Cre-lox site-specific recombination between *Arabidopsis* and tobacco chromosomes" The Plant Journal 23:715-722.

Kozak, "Initiation of Translation in Prokaryotes and Eukaryotes" Gene 234:187-208(1999).

Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant staphylococci on cotton fibers by functional display of a fungal cellulose-binding domain" FEMS Microbiology Letters 195:197-204.

Lopez de Quinto et al. "Parameters Influencing Translational Efficiency in Aphthovirus IRES-Based Bicistronic Expression Vectors" Gene 217:51-56 (1998).

Martinez-Salas, Encarnacion. "Internal Ribosome Entry Site Biology and Its Use in Expression Vectors," Current Opinion in Biotechnology, 10:458-464 (1999).

Matzk et al. (1994) "Improved Techniques for haploid Production in Wheat using Chromosome Elimination" Plant Breeding 113:125-129.

Melchers et al (1974) "Somatic Hybridisation of Plants by Fusion of Protoplasts" Molec. Gen. Genet. 135:277-294.

Michael et al. (1999) "Efficient gene-specific expression of Cre recombinase in the mouse embryo by targeted insertion of a novel IRES-Cre cassette into endogenous loci" Mech. Dev. 85:35-47.

Mizuguchi et al. (2000) "IRES-Dependent Second Gene Expression Is Significantly Lower Than Cap-Dependent First Gene Expression in a Bicistronic Vector" Mol. Ther. 1:376-382.

Monde et al., "Post-Transcriptional Defects in Tobacco Chloroplast Mutants Lacking the Cytochrome b6/f Complex," The Plant Journal, 21(1):61-72 (2000).

Mountford et al. (1995) "Internal ribosome entry sites and dicistronic RNAs in mammalian transgenesis" Trends Genet. 11:179-184.

Niepel et al. (1999) "Identification and Characterization of the Functional Elements within the Tobacco Etch Virus 5' Leader Required for Cap-Independent Translation" J. Virol. 73:9080-9088.

Neunzig et al. "Self replicating vectors as a tool for gene targeting in plants" Experienta 46:A34 (1990).

Owens et al. "Identification of Two Short Internal Ribosome Entry Sites Selected From Libraries of Random Oligonucleotides," PNAS, 98(4):1471-1476 (Feb. 13, 2001).

Pearson et al. "Improved Tools for Biological Sequence Comparison," Proc. Nat'l. Acad. Sci. USA, 85: 2444-2448 (Apr. 1988).

Peterson-Burch et al. "Retroviruses in plants?" Trends in Genetics 16:151-152 (2000).

Porta et al. "Use of Viral Replicons for the Expression of Genes in Plants" Molecular Biotechnology 5:209-221 (1996).

Preiss et al. "Dual Function of the Messenger RNA Cap Structure in Poly(A)-tail-promoted Translation In Yeast," Nature, 392:516-520 (Apr. 2, 1998).

Qin et al. (Mar. 1994) "Cre recombinase-mediated site-specific recombination between plant chromosomes" Proc. Natl. Acad. Sci. 91:1706-1710.

Riera-Lizarazu et al. (1993) "Polyhaploid Production in the Triticeae: Wheat x Tripsacum Crosses" Crop Science 33:973-976.

Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).

Schreuder et al. (1993) "Targeting of a Heterologous Protein to the Cell Wall of *Saccharomyces cerevisiae*" Yeast 9:399-409.

Serino et al., "RNA Polymerase Subunits Encoded by the Plastid rpo Genes are Not Shared with the Nucleus-Encoded Plastid Enzyme," Plant Physiol., 117:1165-1170(1998).

Shepard et al. (1983) "Genetic Transfer in Plants Through Interspecific Protoplast Fusion" Science 219:683-688.

Stanley, J. "Geminiviruses: plant viral vectors" Current Opinion in Genetics and Development 3:91-96 (1993).

Staub et al. (1994) "Extrachromosomal elements in tobacco plastids" Proc. Natl. Acad. Sci. 91:7468-7472.

Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in Chlamydomonas chloroplasts" Plant J. 11:635-648.

Suzuki et al., "Engineering of the rp123 Gene Cluster to Replace the Plastid RNA Polymerase α Subunit with the *Escherichia coli* Homologue," Curr. Genet., 38:218-225 (2000).

Toth et al. (2001) "A novel strategy for the expression of foreign genes from plant virus vectors" FEBS Lett. 489:215-219.

Ueda et al. (2000) "Genetic immobilization of proteins on the yeast cell surface" Biotechnology Advances 18:121-140.

Urwin et al. (2000) "Functional characterization of the EMCV IRES in plants" Plant J. 24:583-589.

Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of Agrobacterium T-DNA in *Arabidopsis thaliana* by transient expression of cre" Plant Molecular Biology 38:393-406 (1998).

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

International Search Report for International Application Serial No. PCT/EP01/11629, mailed Jun. 3, 2002.

International Search Report for International Application Serial No. PCT/EP02/02091, mailed Jun. 19, 2002.

International Search Report for International Application Serial No. PCT/EP 02/07134 dated Jun. 27, 2002.

International Search Report corresponding to PCT/EP02/06464; Date of Mailing: Sep. 30, 2002.

International Search Report for International Application Serial No. PCT/EP02/03476, mailed Oct. 21, 2002.

International Search Report for International Application Serial No. PCT/EP01/14421, mailed Nov. 29, 2002.

International Search Report corresponding to PCT/EP02/03266; Date of Mailing: Feb. 18, 2003.

International Search Report corresponding to PCT/EP02/09843, mailed May 21, 2003.

International Search Report mailed on Jun. 8, 2003 for application No. PCT/EP EP 02/09605.

International Search Report mailed on Jul. 14, 2003 for application No. PCT/EP EP 02/04777.

International Search Report for application No. PCT/EP02/09844, mailed Jul. 15, 2003.

Clelland et al. (1999) "Hiding Messages in DNA Microdots," Nature 399:533-534.

International Search Report corresponding to PCT/EP01/15034; Date of Mailing: Jun. 19, 2002.

Derbyshire et al. "Lightning strikes twice: Intron-intein coincidence" *Proc. Natl. Acad. Sci. USA* 95:1356-1357(1998).

Lustig et al. "Long Poly(A) Tracts in the Human Genome are Associate with the *Alu* Family of Repeated Elements" *J. Mol. Biol.* 180:753-759 (1984).

Wu et al. "Markerless Deletions of *pil* Genes in *Myxococcus xanthus* generated by Counterselection with the *Bacillus subtilis sacB* Gene" *Journal of Bacteriology* 178(19):5817-5281 (1996).

Donson et al. "Systemic expression of a bacterial gene by a tobacco mosaic" *Proc. Natl. Acad. Sci. USA* 88: 7204-7208 (1991).

Murakami et al. "High-level expression of exogenous genes by replication-competent retrovirus vectors with an Internal ribosomal entry site" *Gene* 202: 23-29 (1997).

Attal et al., "The efficiency of different IRESs (Internal Ribosomes Entry Site) in monocistronic mRNAs", *Molecular Biology Reports* 27: 21-26 (2000).

Skulachev et al., "Internal Initiation of Translation Directed by the 5'-Untranslated Region of the Tobamovirus Subgenomic RNA $1_2$," *Virology* 263: 139-154 (1999).

\* cited by examiner

1
GTCGACTGAA TATAATGCGC AAACTGAGGA GAAAACGAGA CAATATGTTC ATGAAACGAG
TGTTAAGTAG AGCGAGCCTG AACAGAGCGA CGCGCAGAGT AATTTGAACG CCGAGAATGA
GCCATGAATG AGTCATAAGC CATGAACATC GCATGACCAG CCTCATCAGC GAATACCTAA
TGAGCAGATG GTTTCATTCT CGCCTTAATT TGCACATCAG ATTTAGAATT C
                                                      231

METHOD OF ENCODING INFORMATION IN NUCLEIC ACIDS OF A GENETICALLY ENGINEERED ORGANISM

CROSS-REFERENCE TO RELATED APPLICATIONS

The present application is a 35 U.S.C. § 371 National Phase Application of International Application Serial No. PCT/EP01/15034, filed Dec. 19, 2001 and published in English as PCT Publication No. WO 02/079481 on Oct. 10, 2002, which claims priority to German Patent Application Serial No. 101 15 507.7, filed Mar. 29, 2001, the disclosures of each of which are incorporated herein by reference in their entireties.

FIELD OF INVENTION

The present invention relates to a method of producing a genetically engineered organism containing an encoded information message that relates to a transgenic sequence in said engineered organism. Tests are provided that allow the selection of an appropriate base sequence for the encoded information message. Further, genetically engineered organisms obtained or obtainable by said method are provided. Methods of analyzing such a genetically engineered organism are also provided.

BACKGROUND OF INVENTION

Genetic engineering is a technical process and as such it is subject to specific rules and regulations that are designed so as to ensure proper technical, ecological and economical environments for the process itself and for the resulting products. Such rules are well established in other fields of technology and, among other purposes, are intended to ensure high quality and reproducibility of the process and resulting products, and to protect the general public, consumers, producers, as well as the environment. Genetically modified (GM) organisms are special products created by humans in that they are self-replicating. Thus, any transgenic material released into the environment has a potential of persisting for a very long time. The scientific community is often accused of being overly fascinated by scientific discovery and recklessly endangering public health and environment by advocating early release of genetically modified organisms, such as GM plants. Since 1994, some 3.5 trillion transgenic plants have been grown in the Americas, and no evidence of ill effects was found. Still, 'good technology practices' concerning the process of genetic manipulation and the transgenic organisms as products are far from being mature, and further efforts should be conducted. One such element of more advanced biotechnological processes is providing proper technical information data, including labeling and registration of the products.

Several groups have advocated to label food products containing GM organisms (GMOs). The recent decision of the European Union to curb the moratorium on transgenic plants is a positive move in the right direction (Schiermeier, Q. 2001, *Nature*, 409, 967-968). However, the states which are de facto behind the moratorium called for additional rules on the tracebility and labeling of GM products.

The labelling of objects including liquid and solid materials, valuable objects etc. with nucleic acid fragments has been disclosed in a number of patents/patent applications (see WO9014441; EP408-424; WO9117265; WO9404918; WO9416902). Two patent applications (WO9617954; WO0059917) claim, in addition to non-living objects, the use of DNA/biopolymers for labelling living objects. However, these publications do not provide the teaching of a secure labeling with regard to transgenic organisms. In particular transgenic plants and animals were genetically engineered in such a way as to separate the functional and technical (informational) part of the DNA insert on a host chromosome. The prior art labelling method does neither address the problem of losing the label during multiple reproductions of the GMO nor the problem of a high frequency of loss or corruption of the information content of the label.

It is therefore a problem of this invention to provide methods which allow an unambiguous and secure genetic labelling of GMOs.

It is another problem of the invention to provide methods which allow the tracing of transgenes and GM organisms released into the environment and products derived therefrom.

SUMMARY OF THE INVENTION

These objects are achieved by a method of producing a genetically engineered organism, comprising (a) incorporating into said organism a functional DNA sequence, and (b) incorporating into said organism a non-functional DNA sequence, wherein said non-functional DNA sequence corresponds to the result of the application of a predefined coding scheme to an information message, said information message being related to said functional DNA sequence, said predefined coding scheme providing a mapping from a plurality of possible information messages into a plurality of DNA sequences.

Further, the mapping from a DNA sequence to an information message is preferably unique while the mapping from an information message to a DNA sequence is preferably non-unique so as to provide for versatility and adjustment of the DNA sequence.

Further, said coding scheme is preferably redundant and/or enables the detection and correction of errors to provide stability of the encoded information for a practically relevant period of time.

Moreover, said functional DNA sequence and said non-functional DNA sequence preferably remain linked during reproduction of the organism for a practically relevant period of time.

The invention further describes a method that allows genetic labeling and tracing of the transgene of interest by adding next to it and linked to it, a specialized DNA sequence which sequence performs only labeling function and has no other functionality.

The invention further describes a method of genetic labeling that does not adversely affect the fitness of the transgenic organism and does not adversely affect the performance of the transgene of interest. Further, the label of the invention (non-functional DNA sequence) is genetically stable and stably linked to the transgene of interest, and poses no measurable ecological risk.

This invention further provides a transgenic organism obtained or obtainable according to this method.

To the best of our knowledge, the transgenic organisms obtained herein and described in this invention are the first genetically modified organisms that are genetically labeled by incorporating into an organism a DNA sequence which has no function whatsoever in the organism other than that of providing technical information about the transgenic material.

Further, vectors for incorporating DNA into an organism according to this method are provided.

A method for analyzing a genetically engineered organism produced according to the method of the invention is provided, said method comprising at least one of the following steps:

(a) employing the PCR method for amplifying the non-functional DNA sequence,
(b) using a probe having a sequence complementary to the non-functional DNA sequence,
(c) using an antibody for the immunological detection of a polypeptide expressed from the non-functional DNA sequence,
(d) sequencing the non-functional DNA sequence, and
(e) reading an information message using said predefined coding scheme.

According to the method of the invention, at least two sequences are introduced into an organism: a functional and a non-functional DNA sequence.

The functional DNA sequence contains a gene or a gene fragment of interest e.g. for conferring the organism with a useful trait. The functionality of the functional sequence corresponds essentially to the reason for genetically engineering said organism.

The non-functional DNA sequence is not required for the function of the organism or for the function of the functional DNA sequence, although it may overlap partially with the functional sequence. The information message is related to the functional DNA sequence in that it contains information regarding the functional sequence. Information regarding the functional sequence may include a date, a place, a producer, a company name, a registration or serial number, a reference to a data base or a data base entry containing further information regarding the functional sequence, a trademark etc. An important purpose of the non-functional sequence is to allow a GMO found in the environment or in the market place to be traced back to the producer, date and place of construction or release etc.

The predefined coding scheme provides a mapping from a plurality of possible information messages into a plurality of DNA sequences. Each possible information message may be mapped into a DNA sequence by the application of the predefined coding scheme. The coding scheme may allow a unique or a non-unique mapping. Preferably, the mapping from a DNA sequence to an information message is unique and the mapping from an information message to a DNA sequence is non-unique. In the broadest sense, this mapping may be any binary relation between the set or plurality of allowable information messages and the set or plurality of DNA sequences or (a) subset(s) thereof.

There are many possible coding schemes conceivable for the purpose of this invention. A particularly straightforward possibility would be that the coding scheme is defined by a code book that associates each possible information message (e.g. a company name) with one or more corresponding DNA sequences. This code book may or may not have any inherent structure. In other embodiments of the invention, a predefined coding scheme (that specifies how a large number of possible information messages are to be mapped into corresponding DNA sequences) is used instead of a predefined code book, that provides the predefined mapping separately for each individual information message. In any case, the number of possible information messages that can be encoded is preferably rather large and may, in some embodiments, be larger than 10 or larger than 1 000 or larger than 100 000.

In a preferred embodiment, the information message consists of a sequence of alphanumeric characters. These may be assigned to bases or multiplets of bases. Preferably, multiplets of bases like dublets, triplets, quartets or quintets are used. Most preferred are base triplets. Advantageously, the muliplet of bases has a higher coding capacity than the number of signs or characters to be encoded. The redundancy of the coding scheme thus obtained provides for higher stability of the encoded information e.g. when analyzing a genetically engineered organism or during organism reproduction, broader versatility and an adjustment of the nucleotide sequence to other circumstances like those related to the genetic engineering of the organism (e.g. restriction sites). In addition to redundancy of the coding scheme, further means exist which are capable of improving the error proofness of the method of the invention by providing detection and/or correction of up to a given number of errors. These include e.g. the use of block codes like binary codes and cyclic codes, interleaving codes, cyclic Hamming codes, and convolutional codes (see e.g. Informatik-Handbuch, eds.: Pechenberger and Pomberger, 2. edition, München, Wien, Hanser Verlag, 1999). The encoded information should be stable over a period of time that is practically relevant.

If multiplets of bases are used to encode signs of the information message, multiple reading frames exist. In this case, more than one reading frame may be used for encoding the information message.

In order to make the method of the invention as broadly applicable as possible, the coding scheme should be generally agreed upon and thus be predefined. Preferably, the agreement of the coding scheme is nation-wide. More preferably, it is supranational. The incorporation of a non-functional DNA sequence according to the invention may then become an international standard which aids in the security of GMOs.

The functional and the non-functional DNA sequences of the genetically-engineered organism according to this invention should be linked and stay so in the process of reproduction of the organism. This can be achieved by physical proximity of said sequences. They should be located on the same chromosome. Preferably, they should be close enough in order to minimize the likelihood of separation during reproduction due to a DNA recombination such as crossing over, over a period of time that is practically relevant. A practically relevant period of time may be roughly defined as 200, preferably 100, and at least 50 generations of the organism. It may be practically useful to have the functional and the non-functional sequence directly in sequence in said organism, optionally separated by a spacer sequence. As noted above, these sequences may overlap partially.

Close proximity is achieved most easily by incorporating the functional and the non-functional sequence into the organism simultaneously. However, the invention also comprises the case wherein the non-functional sequence is incorporated into an organism already genetically engineered preferably by subsequent targeted incorporation of a functional sequence or vice versa.

The non-functional DNA sequence is preferably provided with at least one predefined recognition sequence. The recognition sequence(s) may be located inside the non-functional sequence. Preferably, the non-functional sequence is flanked on at least one side by predefined recognition sequence(s). Said predefined recognition sequence(s) allow for the identification of said non-functional DNA sequence. Most preferably, the non-functional DNA sequence is flanked on both sides by recognition sequences. It may then be analyzed by PCR amplification using primers complementary to said predefined recognition sequences followed by sequencing of the non-functional sequence. Flanking recognition sequences may also be used to determine initiation and/or termination of the non-functional sequence. Further, said predefined recognition sequence(s) may be designed so as to accommodate joint and separate recognition of multiple non-functional DNA sequences in a genetically engineered organism. This is important when multiply genetically engineered or labeled organisms become common.

The recognition or flanking sequence(s) are preferably predefined, i.e. they are generally agreed upon similarly as described above for the coding scheme. The non-functional sequence may then be analyzed and the information message may be read from the base sequence of the non-functional DNA sequence by the application of the coding scheme by anybody of ordinary skill in molecular biology. Alternatively, the presence of the non-functional DNA sequence may e.g. be analyzed using a DNA probe directed to a recognition sequence or to (a portion of) the non-functional sequence itself.

Further means of analyzing the non-functional DNA sequence include the use of an antibody to a polypeptide expressed from said non-functional DNA sequence. In this case, the non-functional sequence may comprises a full expression cassette. Alternatively, said polypeptide may be translated by way of an IRES (internal ribosome entry site) element functional in said organism, from a functionally bicistronic mRNA that encodes both the transgene of interest as well as said polypeptide. By these means, the non-functional sequence may be detected in organisms or in products derived therefrom such as (processed) food.

Analyzing the non-functional sequence may be the mere detection of the presence of a non-functional sequence according to the invention in an organism (e.g. by using a DNA probe) or it may involve the determination or recognition of the base sequence of the non-functional sequence or a portion thereof. Analyzing may further involve the application of the coding scheme in order to decode the non-functional DNA sequence.

The recognition sequence may be added to the non-functional DNA sequence after application of the coding scheme to the information message. Alternatively, the coding scheme may be designed such that a sequence having the function of the recognition sequence is added or incorporated directly to the non-functional sequence upon application of the coding scheme to the information message. In this embodiment, the term non-functional DNA sequence comprises the functions of the non-functional DNA sequence and the function of the recognition sequence.

The method of this invention may be applied to all GMOs. It is however preferred to apply it to higher organisms like higher plants and animals. Among animals, mammals are particularly preferred but humans are excluded. Most preferred are higher crop plants.

This invention further provides a method of encoding an information message in a DNA molecule, comprising incorporating into said DNA molecule a non-functional DNA sequence, wherein said non-functional DNA sequence corresponds to the result of the application of a predefined coding scheme to the information message, said predefined coding scheme providing a mapping from a plurality of possible information messages into a plurality of DNA sequences.

The principles outlined above for said method of producing a genetically engineered organism also apply to this method of encoding an information message in a DNA molecule, when applicable.

Said DNA molecule may be a plasmid or chromosomal DNA. It may be isolated or contained in an organism. Preferably, it may be maintained in an organism. Most preferably, said information message or said non-functional DNA sequence may be a trademark.

Finally, this invention provides a method of labeling a DNA molecule with a trademark, comprising
(a) selecting a nucleotide sequence capable of functioning as a trademark and
(b) incorporating said nucleotide sequence in said DNA molecule such that it may be detected and recognized as a reference to the origin of the DNA molecule.

The method of labeling a DNA molecule with a trademark is a special application of the method of the present invention, whereby the predefined coding scheme maps the nucleotide sequence capable of functioning as a trademark to the proprietor of the trademark.

Vectors for incorporating DNA into an organism according to the method of producing a genetically engineered organism may be designed according to known principles of molecular biology. These vectors should be able to stably introduce a DNA sequence of interest into the genome of an organism. Such vectors may e.g. be of viral origin. In the case of plants, *Agrobacterium tumefaciens*-mediated incorporation of DNA of interest in the plant may for example be used. Several other transformation methods are known in the art like ballistic or particle gun methods.

DETAILED DESCRIPTION OF THE INVENTION

Figure 1:
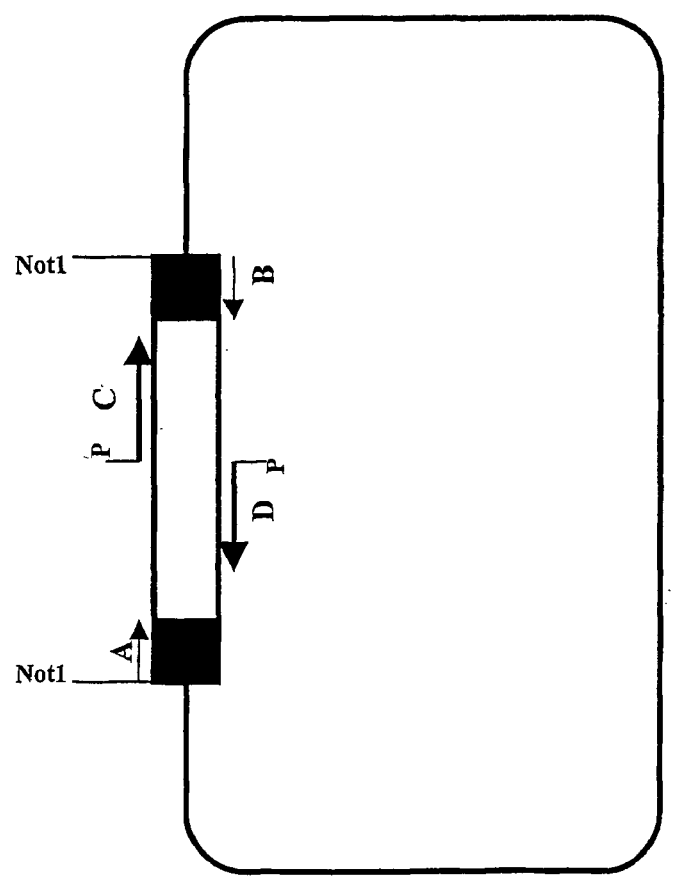
FIG. 1 depicts a vector for encoding and updating of non-biological information. The filled area of the vector corresponds to the conserved regions, designated for amplifying the coding (non-filled) region with primers A and B. Primers C and D are designed for updating/replacing the information within the coding region.

Here, we propose to label GM organisms (GMOS) per se, by including a DNA-encoded (technical) information message in a GMO's genome, preferably next to a functional DNA sequence like a transgene. Such an information message may be based on a non-genetic code or a coding scheme, and it may easily be retrieved and be read. It may store various amounts of information. In a preferred embodiment, such labeling could be adapted as a universal coding standard of GMOs, thus further defining the legal environment in genetic engineering and thereby protecting the public, the environment as well as producers.

Coding Scheme/Languages

The proposed (technical) information of the information message will be encoded in DNA, thus, we are limited to the four-letter DNA storage language. To make the language of the information message as user friendly as possible, English language may be chosen. In this case, a coding scheme that translates the four letters of DNA (A, T, C, G) into a language that has 26 Latin alphabet letters, 10 Arabic numerals and one or two space/stop characters, i.e. a total of 37-38 (alphanumeric) characters. It is obvious that we are being best served by a coding scheme that translates nucleotide triplets, very much like Nature's genetic code. Such a code has the capacity to code for 4³=64 characters, a number that is more than sufficient for the purposes of the invention. The proposed code will thus also be to a certain extent redundant, which minimizes read errors and provides for higher stability during organism reproduction. Further, this allows to avoid the creation of non-functional sequences that contain unwanted features such as restriction sites, complicating the genetic engineering process, or repetitive sequences that may affect the stability of the DNA insert. If the language used is based on English words, the coding scheme becomes even more redundant, as corrupted messages with changed alphanumeric symbols may still be recognized due to the inherent redundancy of natural languages. An example of a coding scheme that takes the above into consideration is given in Table 1. Another example is given in Table 2, wherein triplets that code for the same alphanumeric character differ in all three bases, giving further versatility and means for adjusting the non-functional DNA sequence to circumstances in question.

Most preferably, the coding scheme is degenerate in order to allow encoding of a desired information message or of an alphanumeric character by more than one nucleotide sequences or base multiplet, respectively. The degeneracy of the coding scheme may substantially be increased compared to the use of base triplets by using base quadruplets or quintets. The use of base quadruplets is preferred.

Although we consider a highly-structured coding scheme, such as the scheme that converts triplet codons into alphanumericals to be a preferred coding scheme, other coding schemes that are based on the use of idiosyncratic nucleotide sequences assigned to specific users or database keys, are also contemplated in this invention. Notably, the coding scheme of the invention is by no means restricted to the Genetic Code or analogous coding schemes. The number of coding schemes which can be used according to the principles of the invention is virtually unlimited and includes also the use of two or more different coding schemes which may be combined.

To define a useful message content and length, analogies with other existing products on the market may be made. On the back of a machine, for example a computer, one usually finds data such as name of the maker/company, production date, place of production, product model and serial number. Assuming that the situation in genetic engineering is generally similar (perhaps, we would want to add a name of registered product owner, which may or may not be the producer, and one additional message section that could be reserved for near future), we conclude that a sufficient message length for the near future could be on the order of 3-10 words, each having sufficient coding capacity as to reflect the complexity of the industrial world. However, substantially longer messages are possible as well. The DNA-encoded information would thus give sufficient general information available to everyone, as well as references to information stored on other media, such as a full database of the producer, or a special database of a governmental agency. Assuming average lengths of the words currently used on labels of technical products, we arrive at a total message length of about 100 or so alphanumeric characters corresponding to 300 nucleotides if base triplets are used. However, much longer information messages may also be encoded.

Thus, the non-functional DNA sequence may contain information relevant to the genetically engineered organism produced by the method of the invention. Said product relevant information may comprise information relating to the functional DNA selected from the following group or any other information: a trademark, a reference to a data base, a date, a place, name of the producer or owner, as well as information on the presence and/or position of the functional DNA sequence.

Reading Initiation/Termination

For technically simple and reliable reading of a DNA-encoded information message, one preferably needs convenient and universal initiation and termination signals. Taking into account the current state of the art of DNA manipulation, one is best served by unique sets of short (on the order of 18-30 nucleotides in length) predefined recognition sequences that allow for easy amplification of the message DNA in question (non-functional DNA sequence) and that are preferably widely agreed upon and declared as standard. Amplification primers would thus also allow one to determine the start and the end of the region on the DNA encoding the information message. Said predefined recognition sequences and the respective primers are preferably of sufficient length to be unique in the genetically engineered organism.

The non-functional DNA sequence having said predefined recognition sequence(s) preferably consists of one continuous stretch of DNA. Alternatively, the non-functional DNA sequence may consist of two or more stretches of DNA, i.e. it may be interupted by other DNA sequences. Said non-functional DNA sequence may be interupted by the functional DNA sequence or a part thereof. Thus, the functional DNA sequence may be flanked on both sides by stretches or portions of the non-functional DNA sequence. Further, the predefined recognition sequences of the non-functional DNA sequence may flank the functional DNA sequence such that the functional DNA sequence may be amplified by PCR and analysed by sequencing, optionally together with the non-functional DNA sequence. Such sequencing of the functional DNA sequence may provide further information on the functional DNA sequence. This embodiment may advantageously be combined with the embodiment, wherein the non-functional DNA sequence has two, three or more segments which (i) code for the same information and (ii) have nucleotide sequences which are preferably sufficiently different so as not to cause recombination (see below). The functional DNA sequence may then be flanked by said segments of said non-functional DNA sequences.

Organisms may be genetically modified more than one time, which may result in more than one label or non-functional DNA sequence. The problem of multiple labeling is easily resolved by creating different sets of message initiation sequences, one that is degenerate and will detect all possible starts, and a series of others that are less degenerate or unique. Any decoding by PCR would then start with degenerate sequences and, when multiply modified and labeled organisms become a commonplace, would include multiple less degenerate primers. The conserved regions of the messages shall be long enough to serve as priming sites for PCR analysis, e.g. at least 18 to 20 base pairs. However, unnecessarily long conserved regions might cause unwanted recombination events in the case of multiple messages being located at the same locus.

Genetic Stability of the Message

It is desired that the non-functional DNA sequence for encoding the information message (technical information) remains stable and linked to the functional DNA sequence (e.g. transgene of interest) through generations, and that there is no deterioration of the information quality over a practically relevant period of time. Preferably, the genetic stability of the non-functional DNA sequence is such that the encoded information message persists at least through as many reproductions of the genetically engineered organism as the function of the functional DNA sequence. To fulfill these requirements, the nucleotide sequence of the non-functional DNA sequence, optionally in conjunction with a spacer DNA sequence that may be used between the non-functional DNA sequence and the functional DNA sequence, is preferably chosen so as to exhibit essentially no recombination prone profile, notably in comparison with the genome of host species, and/or to exhibit essentially no deleterious homology to the host genome.

More specifically, the non-functional DNA sequence is preferably engineered such that it is not able to form secondary structures and/or such that it does not contain sequences known as recombination or mutation "hot spots", e.g. "hairpin" structures or palindromes or direct/inverted repeats. Similarly, a DNA spacer sequence which may be used between the non-functional and the functional DNA sequence has to be engineered using the same precautions. To this end, searches of different nucleotide sequence databases may be used (e.g. a Blast Search) to identify any putative "recombination or mutation hot spots" or homology to residential genes or a transgene of the host organism in the non-functional DNA sequence and/or the spacer DNA sequence. An example of such a search is presented in EXAMPLE 3. To further reduce the frequency of a recombination between the non-functional and the functional DNA sequence, the physical distance between the two has to be kept short, preferably as short as technically possible. The distance between the functional and the non-functional DNA sequence should be kept shorter than 10 000 nucleotides, preferably shorter than 1000 nucleotides.

This invention further provides a method of experimentally measuring the recombination frequency and mutability of the non-functional DNA sequence (see EXAMPLE 4). According to this method, the nucleotide sequence of the non-functional DNA sequence, optionally in conjunction with a spacer DNA sequence which may be inserted between the non-functional DNA sequence and the functional DNA sequence, is defined as a member of a set of test sequences identifiable with the following test:

(a) creating DNA molecules each comprising a test sequence between a selectable marker sequence and a counter-selectable marker sequence;
(b) culturing cells transformed with said DNA molecules in the presence of a first agent corresponding to the selectable marker sequence and a second agent corresponding to the counter-selectable marker sequence under conditions where both agents are effective;
(c) isolating cells surviving in step (b);
(d) selecting a test sequence from the cells isolated in step (c) which does not show a significantly increased mutation or recombination frequency compared to other regions of the transformed chromosomes of said cells.

According to this method, two or more non-functional DNA sequences differing in their nucleotide sequences are created for a desired information message making use of the degeneracy of the coding scheme; thus a set of test sequences is created. Each member of the set of test sequences is then subjected to the above test. For said method of producing a genetically engineered organism, a member of said set of test sequences may be selected as non-functional DNA sequence, which exhibits a desired or low recombination frequency and/or mutability. Said test may also be used for identifying a suitable spacer DNA sequence or a suitable combination of non-functional DNA sequence and spacer DNA sequence.

Said test is preferably designed such that the situation in the organism to be genetically modified according to the method of the invention is simulated as good as possible. On the other hand, the long generation times of many multicellular organisms, e.g. one year in the case of many crop species, are preferably avoided. Therefore, said test is preferably performed with cells in cell culture instead of with multicellular organisms. Said test is more preferably carried out with bacterial cells, notably with *E. coli* cells, for reasons of simplicity. However, cells of monocellular plants like *Chlamydomonas reinhardtii* may also be chosen, notably if the organism to be genetically engineered is a plant.

A further possibility of increasing protection of the information message against random missense mutations in the non-functional DNA sequence is to increase the redundancy of the information message e.g. by employing a non-functional DNA sequence having two, three or more segments which (i) code for the same information and (ii) preferably have nucleotide sequences which are sufficiently different so as not to cause recombination. Said segments may be introns. Said segments may be on the same or on different DNA strands and may be read in different orientation. Use of different non-functional DNA sequence segments which have different nucleotide sequences and code for the same information message is permitted by the degeneracy of the coding scheme. A mutation or recombination event corrupting the information message in one of said segments will leave one or more uncorrupted copies of said information message encoded by an unmutated segment.

In EXAMPLE 2, the degeneracy of the coding scheme of Table 1 is employed for duplicating the information message in order to increase the protection level against random "missense" without creating sequence repeats. "Information repeats" (conserved regions) are described which are encoded by imperfect inverted repeats (segments) with 68% sequence identity. However, 32% of mismatches evenly distributed among these repeats make the possibility of interaction between these repeats at physiological conditions close to zero. Use of the information repeats allows to detect the great majority of the potential DNA mutations: both nucleotide substitutions as well as internal deletions.

By using the coding scheme exemplified in Table 2, the sequence identity of information repeats can further be reduced while increasing the overall freedom and versatility to encode the information message. A particularly high degeneracy of the coding scheme can be obtained if base quadruplets are used to code for alphanumeric characters.

Another alternative contemplated here is the use of different codes for generating "information repeats", thus avoiding the creation of any nucleic acid repeats at all. The use of information repeats can be easily accommodated as the overall length of the message is fully within technically manageable limits.

A further possibility of increasing the error proofness of the information message is the use of multiplets of, preferably, identical bases instead of a single base. As an example, the base sequence GGGCCCGGG may be used instead of the base sequence GCG for encoding the character B according to Table 1. Doubling, triplicating or quadruplicating of a base are preferred alternatives of this embodiment. Triplicating is preferred. Such a coding scheme has the advantage that point mutations which may occur in the course of reproduction of the genetically engineered organism may be easily identified and corrected upon decoding of the information message from the non-functional DNA sequence. Further, the reading frame of the non-functional DNA sequence is easy to identify even if a frame shift due to insertion or deletion mutations has occurred.

In a further preferred embodiment, the non-functional DNA sequence may be designed as an intron or an intein. Introns are preferred. Said intron or intein may be situated preferably within the related functional DNA sequence. It may be placed within a highly conserved or a functionally most crucial portion thereof, which is most protective, notably for preserving the linkage between the functional and the non-functional DNA sequence. It is also possible to use several (e.g. three) different introns with different base sequences but preferably coding for the same information message as allowed by the coding degeneracy. The predefined recognition sequences that may be used for PCR amplification of the non-functional DNA sequence may be part of said introns. Methods of engineering group I and group II introns are known in the art. Details may be found in the following documents and in references cited therein: Ayre et al. (1999) Proc. Nat. Acad. Sci. USA 96, 3507-3512; Valadkhan and Manley (2001) Nature 413, 701-707; Hagen and Cech (1999) EMBO J. 18, 6491-6500; U.S. Pat. No. 6,143,503; U.S. Pat. No. 6,010,904; U.S. Pat. No. 6,015,794). In the case of an intein as non-functional DNA sequence, the expressed non-functional DNA sequence or a portion thereof is a polypeptide and may be detected with an antibody. A set of specific antibodies each of which can recognise a predefined polypeptide may be provided e.g. as a kit-of-parts. Each detected polypeptide-antibody reaction may stand for an information message previously agreed upon. Methods of engineering inteins are known in the art. Details may be found in the following documents and references cited therein: Lew et al. (1998) J. Biol. Chem. 273, 15887-15890; Liu (2000) Annu. Rev. Genet. 34, 61-76; Kenneth et al. (1998) Proc. Natl. Acad. Sci. USA 95, 3543-3548).

In the process of the invention, said incorporation into said organism of said non-functional DNA sequence should not adversely affect the genetic stability of the non-functional and/or the functional DNA sequence and/or the linkage between the non-functional and the functional DNA sequence. To this end, an experimental test is provided, wherein the non-functional DNA sequence is defined as a member of a set of test sequences identifiable with the following test:

(a) creating DNA molecules comprising said functional DNA sequence with said non-functional DNA sequence connected to the functional DNA sequence optionally via a spacer DNA sequence;

(b) introducing said DNA molecules into cells to create transgenic cells and transgenic organisms comprising said functional DNA sequence connected to the non-functional DNA sequence optionally via a spacer DNA sequence;

(c) analyzing the performance of said functional DNA sequence connected to the non-functional DNA sequence, optionally via a spacer DNA sequence, said performance being defined by expected regular Mendelian segregation of said sequence among the sexual progeny and by the maintenance of full linkage between said functional DNA sequence and said non-functional DNA sequence in the process of sexual reproduction of said transgenic organisms, and (d) identifying a non-functional DNA sequence optionally with a spacer DNA sequence that does not affect the genetic stability of said functional DNA sequence or the genetic linkage between the non-functional DNA sequence and functional DNA sequence Biological Neutrality/Ecological Safety of the Non-Functional DNA Sequence A. Effect of the Non-Functional DNA Sequence on the Performance of the Functional DNA Sequence (Transgene)

The physical proximity of the non-functional DNA sequence and the DNA encoding the transgene of interest (functional DNA sequence) may affect the performance of the transgene of interest in the genetically engineered organism in many ways, most of which would not be desirable. Some of the parameters that are of special interest in this regard include: genetic stability of the combined DNA insert; direct or indirect effect of the non-functional DNA sequence on transcription and translation of the transgene of interest, in particular inhibition of the expression level; potential for triggering silencing of the transgene, etc. Most of these effects can be monitored/measured by direct evaluation of two groups of transgenic organisms: (a) those that have both the transgene of interest as well as the non-functional DNA sequence, optionally including a spacer in between, and (b) those that have the transgene only. To avoid most of the problems of this kind, here too, searches of sequence databases should be performed beforehand, in order to minimize inadvertant creation of sequences such as those that mimic viral sequences known to trigger silencing in eukaryotes. In special cases, the spacer and the non-functional DNA sequence may even have a desirable effect, e.g. a function as expression enhancer or insulator.

Further, this invention provides an experimental test for analysing the effect of the non-functional DNA sequence on the performance of the functional DNA sequence comprising the following steps:

(a) creating DNA molecules comprising said functional DNA sequence (i) without and (ii) with said non-functional DNA sequence connected to the functional DNA sequence optionally via a spacer DNA sequence;

(b) introducing said DNA molecules into cells to create transgenic cells and transgenic organisms comprising said functional DNA sequence (i) without and (ii) with said non-functional DNA sequence connected to the functional DNA sequence optionally via a spacer DNA sequence;

(c) comparing the performance of said functional DNA sequence in the two sets of transgenic cells and/or transgenic organisms, said performance being defined by at least one of the following parameters: transcription and translation capability, translation level, silencing sensitivity, sequence mutability; and (d) identifying a non-functional DNA sequence, optionally with a spacer DNA sequence, that does not affect the performance of said functional DNA sequence.

Using the degeneracy of the coding scheme, several non-functional DNA sequences differing in their nucleotide sequence but coding for the same desired information message may be created. The non-functional DNA sequence exhibiting the most suitable properties in the above test may be selected for said process of producing a genetically engineered organism.

This test is preferably carried out with cells and/or organisms of the species to be genetically engineered by the process of the invention. If long generation times of the organisms of said species are to be avoided, said test may be carried out in cell culture.

B. Genetic and Physiological Neutrality of the Non-Functional DNA Sequence

In this invention, the presence of the non-functional DNA sequence should not adversely affect the biological fitness of the genetically engineered organism containing it. In a preferred embodiment of the invention, the non-functional DNA sequence should not be expressed, e.g. transcribed and/or translated (except for the cases when we do want the technical message to be translated into a polypeptide or at least to be transcribed). In order to avoid any translation, we propose to flank non-functional DNA sequence by six translation stop codons (three per each DNA strand, one for each reading frame), thus making the creation of a translation product impossible even if the non-functional DNA sequence will be transcribed by a "leaky" transcription process. It is advisable to use searches against different available sequence databases, e.g. by a Blast Search for the presence of any putative promoters, transcriptional or translational enhancers or homology to residential genes and transgenes in the non-functional DNA sequence. In EXAMPLE 3, the search is performed in order to avoid the presence in the non-functional DNA sequence of homology to a host RNA fragment complementary to a resident mRNA that could inadvertently affect the expression of a residential gene and consequently the fitness of the host. However, the database search is mostly restricted to organisms with completely sequenced genomes and the search results might not detect all existing homologies for other organisms. To address this problem, the non-functional DNA sequence can also be used as a hybridization probe for Southern- or dot-blot hybridization analysis of host DNA at different conditions of different stringency (Sambrook, Fritsch & Maniatis, 1989, Molecular Cloning, Cold Spring Harbor Laboratory Press, N.Y.).

Further an experimental test analogous to that described above under (A) may be performed in order to identify undesired effects of the non-functional DNA sequence on the biological fitness of the genetically engineered organism. The performance of said transgenic cells and/or transgenic organisms is evaluated by at least one of the following parameters in step (c): yield, general productivity, resistance to biotic and abiotic stresses etc.

C. Ecological Safety

The modifications contemplated in this invention should result in genetically engineered organisms that have no components of properties that would make them ecologically dangerous or unsafe. Probability of such an inadvertent effect is extremely remote, because the relatively short length of the DNA practically needed for technical labeling, makes it unlikely that said non-functional DNA sequence will change the performance of the organism so dramatically as to create an ecologically superior pest or "superweed". Also, the lengths of the non-functional DNA sequence contemplated in this invention are too short to be able to manifest any independent genetic or biological function in an organism (such as to function as a promoter or to become a self-replicating entity, a virus-like vector), or to acquire such functions upon horizontal transfer from one class of biological organisms to another.

This invention provides an experimental test for assessing the ecological safety of the non-functional DNA sequence. This test may be carried out in an analogous way to the tests described above under item (A) and (B). The performance of said transgenic cells and/or organisms is compared in step (c), said performance being defined by at least one of the following parameters: outcrossing preference with the local landraces of the same species or related weed species. Said test is preferably carried out with plants in a greenhouse.

Technical Considerations

Technically, the synthesis of a coding stretch of DNA (non-functional DNA sequence) can be executed gradually by using sets of overlapping primers. This does not require the synthesis of very long primers and may be performed in any standard molecular biology laboratory. The final PCR product, preferably flanked by two rare-cutting restriction sites (e.g. Not1), can be cloned in a small high-copy plasmid vector (e.g. pUC or pBS family), as is shown in FIG. 1. In this vector, the information message encoded in the stretch of DNA can be easily updated by using two phosphorylated custom primers, non-overlapping but starting from the same position in two opposite orientations (primers C and D, FIG. 1). These primers may introduce all necessary changes into the coding stretch. The PCR product carrying such changes can be treated with Klenow fragment of DNA polymerase 1, religated and transformed into E. coli. The coding stretch can be easily recloned into any vector of interest using standard molecular biology techniques. The stretch of DNA encoding non-biological information can be detected in a genetically modified organism (or even product from such organism, as it always has traces of DNA) by using primers complementary to the flanking recognition sequences of the non-functional DNA sequence (primers A and B, FIG. 1). Taking into account that a mismatch with the template at the 3' end of the primer does not allow the PCR to proceed, extension of primers A and B into the variable coding core region (of the non-functional sequence) allows the detection of two or more different labels in the same GMO or its derivative. The PCR products can be subcloned or sequenced directly and the non-biological information decoded, thus allowing the identification of a GM, also in a GMO-derived product.

To further facilitate the detection of a GMO, the region encoding the information message may also encode a segment containing information that is expressible by the living organism's genetic machinery. Such information can, after transcription and translation, produce a short universal polypeptide easily detectable by fast and sensitive immunological techniques and being indicative of the transgenic nature of the organism in question. In this approach, the issues such as biological neutrality of the added polypeptide should be addressed beforehand, very much as outlined in the previous paragraphs.

In summary, biological neutrality/ecological safety and genetic stability of the message can be addressed by the method of design and sequence analyses described above and in EXAMPLES 3 and 4. The technical message can also undergo additional tests usually required for transgenic organisms. Said tests usually have a high degree of similarity and the differences depend very much on the nature of the transgenes to be tested, for example, a plant that resists herbicides is evaluated differently than a plant that is protected against insect pests. An effect of the non-functional DNA sequence on transgene expression can be evaluated by simple comparison of transgenic organisms that differ only by the presence/absence of technical message. Assessments by product developers are conducted in accordance with principles developed by environmental experts around the globe (U.S. National Research Council, 1989, *Field Testing Genetically Modified Organisms: Framework for Decisions*. Committee on Scientific Evaluation of the Introduction of Genetically Modified Microorganisms and Plants into the Environment. National Academy Press, Washington, D.C.; Organization for Economic Cooperation and Development, 1992, *Safety considerations for biotechnology*, OECD, Paris, 50 pp.; Government of Canada, 1994, *Assessment criteria for determining environmental safety of plants with novel traits*. Dir9408, Dec. 16, 1994. Plant Products Division, Plant Industry Directorate, Agriculture and Agri-food Canada). Results of these assessments are sent to EPA, USDA, the Food and Drug Administration and other regulatory bodies around the world, who evaluate the data in determining whether a biotech product should ultimately be approved for marketing. Different parameters can be included in such assessments.

For example, a standard data package reviewed by the Animal and Plant Health Inspection Service (APHIS) of US Department of Agriculture typically includes information in the following areas:

Compositional analysis. Researchers look for any change in the plants' composition or physiology that could have an ecological effect. An increase in existing toxicants, for example, would raise concerns about wildlife that could feed on the crop.

Germination/dormancy. These studies, done in a wide range of temperature regimens, examine whether the biotech seed differs from the conventional seed. A seed with increased dormancy, for example, might have an increased ability to survive in soil over winter, which could lead to a negative effect such as weediness.

Seed bank longevity. These studies determine if the seed survives at various depths in soil, storage or in a reference collection.

Growth and reproduction. Various characteristics of growth and reproduction of the biotech plant and the conventional plant are compared. Corn, for example, would be examined for early stand count, days to pollen shed, days to silking, ear height, plant height, days to maturity, number of dropped ears, grain moisture, test weight, yield, and other factors. Many of these characteristics are routinely evaluated for new plant varieties. Any differences would be assessed to determine if they could give the modified plant an ecological edge or affect wildlife.

Outcrossing. These crop-specific assessments examine whether the insertion of a new gene increases the ability of the plant to become a weed. For example, soybean has no wild relatives in the US, so outcrossing to wild relatives is not an issue in the U.S. for new soybean varieties developed through biotechnology. In cases where compatible wild plants exist, APHIS considers whether the transfer of a specific trait, such as insect protection, would give the wild plant an advantage over other plants. Also, based on APHIS assessment, EPA has prohibited the planting of Bt crops in isolated geographic regions where outcrossing to wild relatives is considered possible (e.g. wild relatives of cotton in Hawaii). In view of the recent data that demonstrated a transfer of maize transgenes from transgenic varieties to traditional landraces in Mexico (Quist & Chapela, *Nature,* 414, 541-542 (2001), specific evaluation of the outcrossing pattern may also be important.

Assessment of fitness. Many agricultural crops, because of years of traditional crossbreeding, are not fit to survive outside of a highly managed agricultural environment. In assessing a biotech crop, APHIS considers whether the insertion of a gene would improve the plant's ability to become established and outcompete wild vegetation, in other words, to become a weed.

Allelopathic potential. In nature, some plants may have a herbicidal effect on other plants. APHIS examines whether inserting a new gene into a crop gives it such allelopathic ability.

Field observations. Multiple years of field trials at multiple sites provide opportunities to observe any unexpected effects on soil, water, wildlife or other plant life. However, we believe that the non-functional DNA sequence of the invention itself will not require such a thorough analysis, as its expression on RNA/protein level can be efficiently controlled by the design of said sequence. Usually, a required test of transgenic organism will also serve as test for non-functional DNA sequence. Toxicology studies might be necessary only in specific cases of non-functional DNA sequences that can be translated into a product.

This invention further provides a method of detecting members of a set of diversely genetically engineered organisms, whereby said set is defined as follows:
(i) each member contains at least one functional DNA sequence;
(ii) different members contain different functional DNA sequences;
(iii) each functional DNA sequence is flanked at its upstream side by a first predefined recognition sequence and at its downstream side by a second predefined recognition sequence,
(iv) all first predefined recognition sequences in said set are identical;
(v) all second predefined recognition sequences in said set are identical;
(vi) said first and said second predefined recognition sequences are adapted for PCR amplification of said functional DNA sequence;
(vii) said functional DNA sequence and said non-functional DNA sequence remain linked during reproduction of the organism for a practically relevant period of time;

whereby said method is characterized by the following steps:
(a) subjecting a DNA sample of said genetically engineered organism to PCR amplification using primers corresponding to said first and second predefined recognition sequences to obtain a PCR product;
(b) determining whether or not a PCR product is obtained in step (a);
(c) interpreting a positive result of step (b) as evidence for the presence of a member of the above-defined set in said sample; and
(d) optionally sequencing the PCR product of step (a) for identifying the functional DNA sequence.

This method allows to detect different genetically engineered organisms by PCR amplification using the same primers. Said PCR allows to amplify a transgene that is flanked on both sides by pre-defined recognition sequences. The formation of a PCR product identifies the organism genetically endowed with a transgene. Said transgene may be identified by sequencing the PCR product. Said pre-defined recognition sequences are preferably generally agreed upon, as described for said method of producing a transgenic plant. Pre-defined recognition sequences of identical sequence are used as flanking sequences of a transgene in a set of diversely genetically engineered organisms. Each of said predefined recognition sequences preferably has a negligible chance of occurring naturally in the genome of an organism. The members of said set preferably differ in that they contain different transgenes. Alternatively or additionally, said members of said set may further differ in that they belong to different taxonomic families, to different genera but to the same family, to different species but to the same genus, or to different varieties but to the same species. If said members belong to the same species they are modified with different transgenes. The organisms of this method are preferably plants, notably higher crop plants. Use of identical pre-defined recognition sequences in diversely genetically engineered organisms allows the use of the same primers for detecting a member of said set.

Also, genetically engineered organism detectable by said method of detecting are provided.

TABLE 1

PROPOSED CODON USAGE FOR ENCODING ENGLISH ALPHABET AND NUMBERS

| Character | Triplet codons | |
|---|---|---|
| A | GAT | |
| B | GCG | GCA |
| C | GTC | GTT |
| D | AGT | AGC |
| E | GCC | GCT |
| F | AAA | AAC |
| G | ACG | ACA |
| H | TGT | TGC |
| I | ACC | ACT |
| J | CCG | CCA |
| K | TAT | TAC |
| L | TCG | |
| M | CCT | CCC |
| N | TCC | TCT |
| O | GTG | |
| P | GTA | |
| Q | CGC | |
| R | AGA | AGG |
| S | ATA | |
| T | ATC | ATT |
| U | CTG | CTA |
| V | CTC | CTT |
| W | TTG | |
| X | TTA | |
| Y | TAA | |
| Z | TAG | |
| "space" | ATG | TTC |
| 0 | CAT | CAC |
| 1 | CAA | CAG |
| 2 | AAT | AAG |
| 3 | GAA | GAG |
| 4 | TGA | TGG |
| 5 | CGT | CGA |
| 6 | GGT | TTT |
| 7 | GGC | GAC |
| 8 | GGA | TCA |
| 9 | CGG | GGG |

TABLE 2

PROPOSED CODON USAGE FOR ENCODING ENGLISH ALPHABET AND NUMBERS

| Character | Triplet codons | |
|---|---|---|
| A | GAT | |
| B | GCG | AGC |
| C | GTC | CGA |
| D | AGT | GCA |
| E | GCC | AGG |
| F | AAA | TGC |
| G | ACG | CTA |
| H | TGT | CCC |
| I | ACC | GTT |
| J | CCG | TAC |
| K | TAT | CCA |
| L | TCG | |
| M | CCT | TTC |
| N | TCC | CAG |
| O | GTG | |
| P | GTA | |
| Q | CGC | |
| R | AGA | GAG |
| S | ATA | |
| T | ATC | TCT |
| U | CTG | ACT |
| V | CTC | GCT |
| W | TTG | |
| X | TTA | |
| Y | TAA | |
| Z | TAG | |
| "space" | ATG | CAC |
| 0 | CAT | GGG |
| 1 | CAA | TTT |

TABLE 2-continued

PROPOSED CODON USAGE FOR ENCODING ENGLISH
ALPHABET AND NUMBERS

| Character | Triplet codons | |
| --- | --- | --- |
| 2 | AAT | TGG |
| 3 | GAA | CTT |
| 4 | TGA | ATT |
| 5 | CGT | AAG |
| 6 | GGT | TCA |
| 7 | GGC | ACA |
| 8 | GGA | AAC |
| 9 | CGG | GAC |

Example 1

Coding Protocol

The biological code proposed in the Table 1 can be used to encode information of non-biological character. Considering that there are at least 37 alphanumeric characters to be encoded (26 alphabet letters in case of the English language, one space sign and 10 numbers) and only 64 triplet codons are available, the choice of designation of one or two codons to the character is based on the expected frequency of use for the specific character. As a result, some letters have only one triplet codon. The space sign has two codons as the most frequently used character. However, we would recommend to use the first codon of the space sign (ATG) at the start of encoded information and the second codon (TTC) at the end of encoded information. The choice of the space sign at the middle of encoded information shall be of free choice and the preference can only be dictated by the necessity to avoid the creation of restriction sites or other unwanted sequences.

Example 2

Generation and Analysis of Transgenic Plants Carrying the Information of Non-Biological Character In this example, the coding scheme of Table 1 is employed. A synthetic DNA was synthesized by the company Genart (Regensburg, Germany) as a "ligation-product". The translated product reads: "I.CAN.GENETICS.NEC.VERO. TERRAE.FERRE.OMNES.OMNIA.POSSUNT"—followed (in a frame in opposite direction) by "SCITENEG.NAC.I". The translation from Latin of NEC.VERO.TERRAE.FERRE. OMNES.OMNIA.POSSUNT" means "Neither can every soil bear every fruit" (Vergil, "Georgica", 2, 109). The two flanking sequences of identical text ("I.CAN.GENETICS") encoded on both strands of DNA represent conserved part of sequence encoding technical information.

Figure 5:
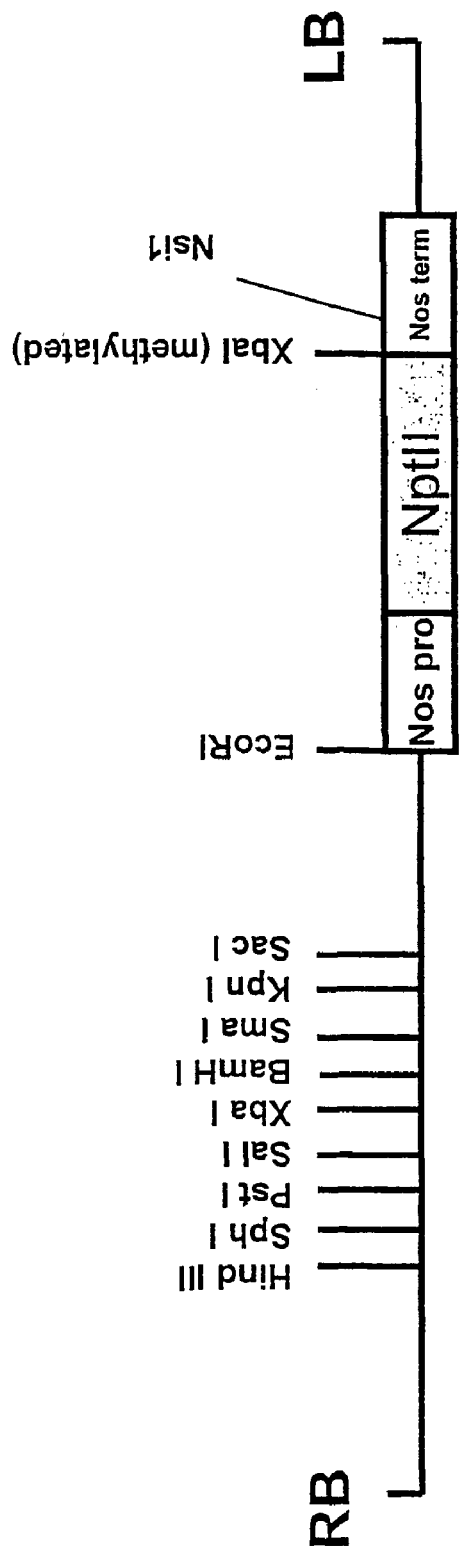
FIG. 5 depicts binary vector pICBV10.

The ligation product (which consists of a PCR product of assembled oligos) was cloned as a BamHI-EcoRI fragment in pICBV10 (FIG. 5), resulting in plasmid pIC4100. The insert was checked by sequencing. The plasmid was immobilised into Agrobacterium strain GV3101 and used for transformation.

Figure 2:
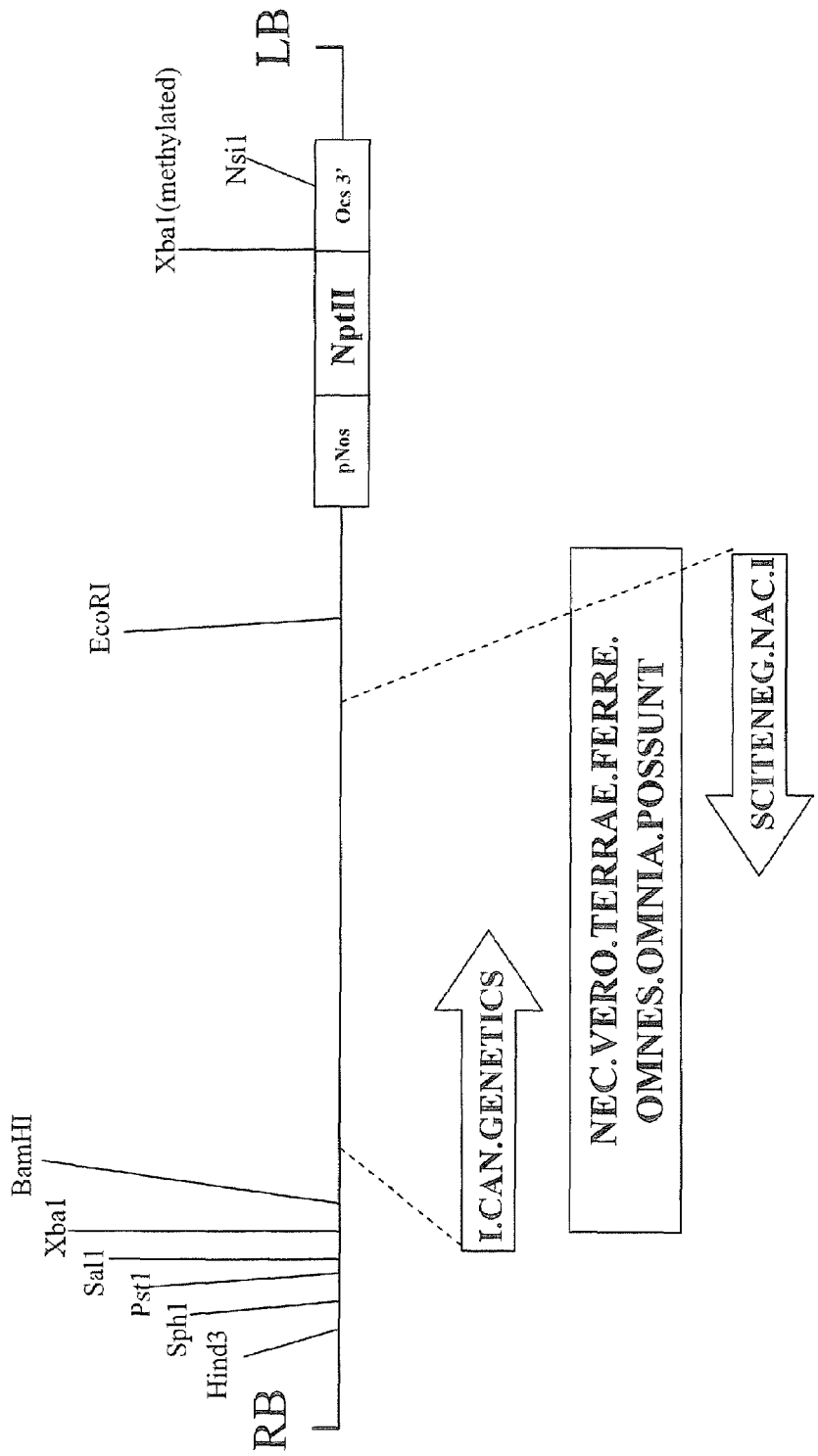
FIG. 2 depicts vector pIC4100 encoding non-biological information for the transformation of plants.

The T-DNA of plasmid pIC4100 (FIG. 2) was introduced in Arabidopsis thaliana (Col-0) plants as descried by Bent et al., (1994, Science, 285, 1856-1860). Seeds were harvested three weeks after vacuum-infiltration, sterilised and screened for transformants on GM+1% glucose medium (Valvekens et al., 1988, Proc. Natl. Acad. Sci. USA, 85, 5536-5540.) containing 50 mg/L kanamycin. The T-DNA of pIC4100 was also introduced into Nicotiana tabacum using an Agrobacterium-mediated leaf disc transformation protocol (Horsh et al., 1985, Science, 227, 1229-1231). Transgenic tobacco plants were recovered by applying kanamycin selection. The transformation of Arabidopsis thaliana and Nicotiana tabacum was also performed with plasmid pICBV10 (FIG. 5), which contains selectable marker but no DNA-encoded technical message. Twenty primary transformants were obtained per construct for each plant species (in total 80 transgenic plants) and used for comparative analysis in order to determine the effect of the DNA-encoded technical message on plant fitness, transgene expression, stability, etc. The transformation experiments with two different plasmids (pIC4100 and pICBV10) were performed in parallel, using the same plant material grown under identical conditions. The selection for transformants was also carried out under identical conditions for control (pICBV10) and tested (pIC4100) plasmids. The experiments demonstrated that the frequency of transformation was comparable for control and tested vectors. Also there were no phenotypical differences between the control plants and plants carrying the technical information. This demonstrates that there is no detectable effect of the DNA encoding technical information on the transformation frequency and plant fitness compared to control plants.

We also tested the stability of the DNA encoding technical information within bacterial and plant hosts. The following set of primers was used to amplify a 231 bp DNA fragment:

F1 (5'-GTC GAC TGA ATA TAA TGC GCA MC TG-3') (SEQ ID NO: 1)

R1 (5'-GM TTC TAA ATC TGA TGT GCA MT TAA GG-3')) (SEQ ID NO: 2)

As a template for PCR were used 1 µl of bacterial suspension or small piece of plant tissue per 50 µl of PCR mixture. The plant tissue for PCR was prepared as described by Klimyuk & colleagues (1993, Plant J., 3, 493-494). The E. coli suspension was taken for PCR after two hours of growth in freshly inoculated LB media with appropriate selection (50 µg/ml carbenicillin). The Agrobacterium suspension was taken from an overnight culture (LB with 50 µg/ml Rifampicin, 50 µg/ml carbenicillin). The PCR conditions were as follows: 94° C. for 20 sec; 60° C. for 20 sec; 72° C. for 1 min; 35 cycles.

Despite the presence of imperfect inverted repeats flanking the message, the DNA fragment of interest was detected in all analysed clones of E. coli and Agrobacterium tumefaciens as well as in all primary transformants carrying pIC4100 T-DNA (20 tobacco and 20 Arabidopsis primary transformants were analysed). Sequence analysis of the PCR products from plant tissue was carried out. No mistakes were detected in the DNA encoding the message. The same sequence analysis was also carried out using PCR products from self-progeny of two *Arabidopsis* primary transformants. No changes in DNA sequence were detected.

Example 3

Figure 3:
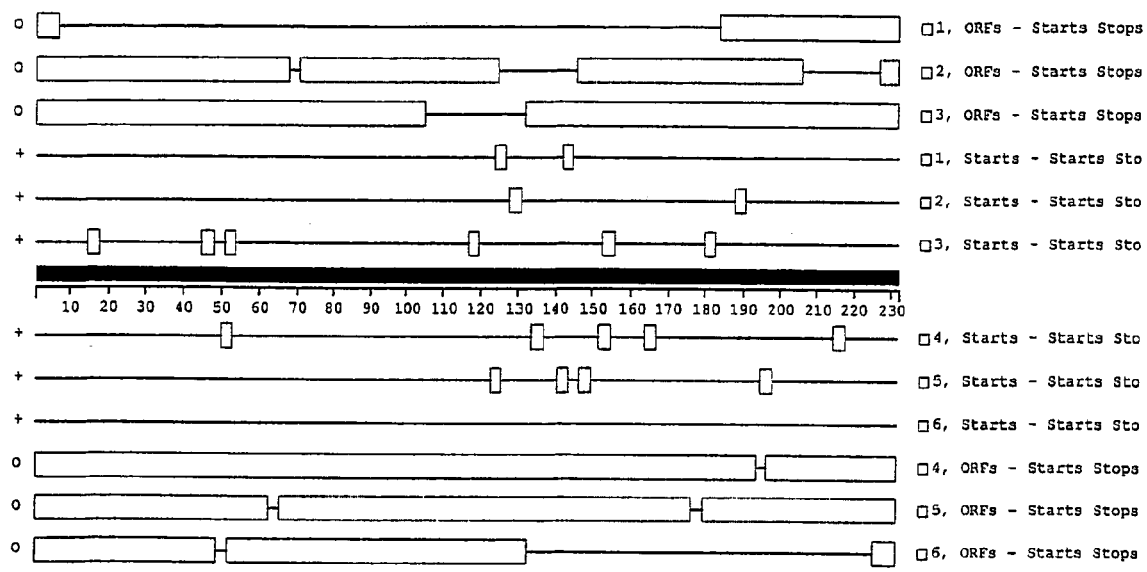
FIG. 3 shows the sequence from vector pIC4100 (SEQ ID NO: 3) encoding non-biological information with schematic presentation of start-stop ORFs (DNASTAR program).

Analysis of DNA Encoding Technical Information for the Presence of Undesired Sequences The simplest way to detect the presence of sequences which are identical/similar to the sequences in the databases is to perform a blast search. We used the sequence shown in FIG. 3 to search against public databases. The results of BlastN and BlastX searches are presented in Appendix 1. The BlastN search results revealed the presence of short stretches of DNA sequences (19-21 bp) identical to the sequences from mammals (cDNA sequences), *Drosophila melanogaster* and *Aspergillus parasiticus*. However, no homology was detected to plant DNA sequence. Only BlastX search revealed a significant homology to an *Arabidopsis thaliana* hypothetical protein and encompasses the DNA stretch encoding for 41 amino acid residues. However, this stretch for technical DNA contains three stop codons disrupting the continuity of the putative translational product at different positions, thus making the synthesis of an artificial protein with homology to an *Arabidopsis* hypothetical protein impossible.

Example 4

Figure 4:
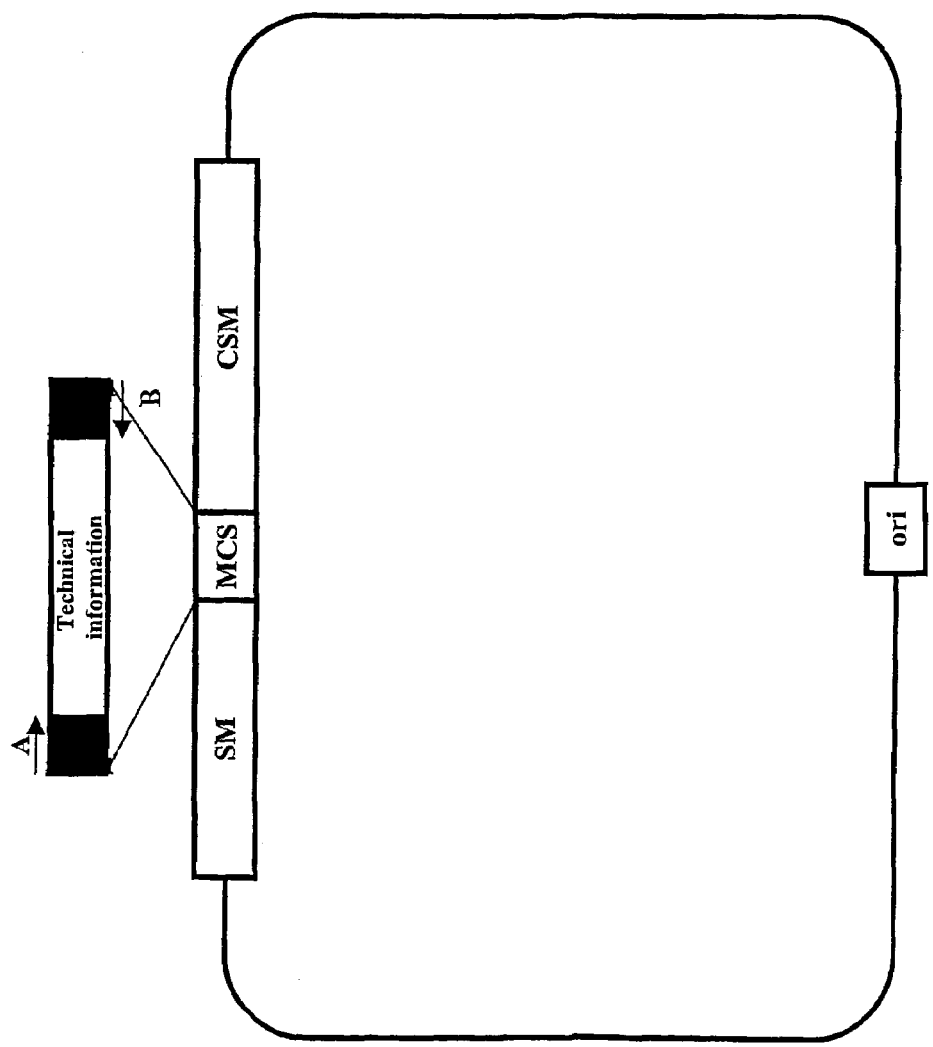
FIG. 4 depicts a vector for testing the recombination frequency within DNA encoding technical information.
  SM—selectable marker;
  CSM—counter-selectable or negative selection marker;
  MCS—multiple cloning sites;
  A and B—PCR primers for amplifying "technical" DNA.

Measurement of Recombination Frequency within the DNA Encoding Technical Information It is advisable to measure the recombination frequency in the region encompassed by the DNA encoding technical information and the linker DNA separating the DNA with technical information from a transgene(s) like a functional DNA. This can help to avoid accidental creation of any recombination "hot spots". The general scheme of a construct designed for such a purpose is shown in FIG. 4. The DNA sequence to be tested can be inserted between a selectable marker (gene conferring resistance to antibiotics) and a counter-selectable marker (conditionally lethal gene conferring sensitivity to a chemical compound). Any bacterial gene conferring resistance to antibiotics (ampicillin, gentamicin, tetracycline, kanamycin, neomycin, hygromycin, etc) could be chosen to serve as selectable marker. As a choice of the counter selectable marker, the *Bacillus subtilis* sacB gene conferring sucrose sensitivity can be used (Steinmetz et al., 1983, *Mol. Gen. Genet*, 191, 138-144; Recorbet et al., 1993, *Appl. Envirol. Microbiol.*, 59, 1361-1366). The recombination events can be selected by growing bacteria on media containing the appropriate antibiotic and sucrose. Only bacterial cells will survive, which have lost through recombination or have an inactive (mutant) form of the sacB gene. Such surviving colonies can be used for PCR analysis (primers A and B, FIG. 4) in order to check the frequency of recombination events with involvement of the DNA fragment encoding technical information. This frequency can be compared with the recombination frequency in the remaining part of the vector in order to determine the presence of a recombination "hot spot" within the analyzed region.

APPENDIX 1

BlastN search

| Sequences producing significant alignments: | Score (bits) | E Value |
|---|---|---|
| gi\|16877788\|gb\|BC017130.1\|BC017130 *Mus musculus*, clone MGC: | 42 | 0.21 |
| gi\|13435767\|gb\|BC004742.1\|BC004742 *Mus musculus*, clone IMAG | 42 | 0.21 |
| gi\|971274\|dbj\|D32249.1\|RATNDAP1 *Rattus norvegicus* mRNA for | 42 | 0.21 |
| gi\|16604068\|gb\|AC097466.2\| *Homo sapiens* chromosome 4 clone | 38 | 3.2 |
| gi\|15451474\|gb\|AC009343.8\| *Drosophila melanogaster*, chromos | 38 | 3.2 |
| gi\|10727654\|gb\|AE003828.2\|AE003828 *Drosophila melanogaster* | 38 | 3.2 |
| gi\|3900825\|gb\|AC005991.1\|AC005991 *Aspergillus parasiticus* c | 38 | 3.2 |

Alignments

\>gi\|16877788\|gb\|BC017130.1\|BC017130 *Mus musculus*, clone MGC: 27629
IMAGE: 4506259, mRNA, complete cds
Length = 2595
Score = 42.1 bits (21), Expect = 0.21
 Identities = 21/21 (100%)
 Strand = Plus/Minus Query:  208  atttgcacatcagatttagaa   228  (nucleotides 208-228 of SEQ ID NO:1)
             |||||||||||||||||||||
Sbjct:  2112 atttgcacatcagatttagaa  2092

\>gi\|13435767\|gb\|BC004742.1\|BC004742 *Mus musculus*, clone IMAGE: 3499845, mRNA, partial cds
Length = 1688
Score = 42.1 bits (21), Expect = 0.21
 Identities = 21/21 (100%)
 Strand = Plus/Minus Query:  208  atttgcacatcagatttagaa   228  (nucleotides 208-228 of SEQ ID NO:1)
             |||||||||||||||||||||
Sbjct:  1216 atttgcacatcagatttagaa  1196

\>gi\|971274\|dbj\|D32249.1\|RATNDAP1 *Rattus norvegicus* mRNA for neurodegeneration associated APPENDIX 1-continued

```
protein 1, complete cds
Length = 4758
 Score = 42.1 bits (21), Expect = 0.21
 Identities = 21/21 (100%)
 Strand = Plus/Minus Query:    208  atttgcacatcagatttagaa   228  (nucleotides 208-228 of SEQ ID NO:1)
               |||||||||||||||||||||
Sbjct:   2338  atttgcacatcagatttagaa  2318

>gi|16604068|gb|AC097466.2| Homo sapiens chromosome 4 clone RP11-26A2, complete sequence
Length = 170321
 Score = 38.2 bits (19), Expect = 3.2
 Identities = 19/19 (100%)
 Strand = Plus/Plus Query:    131  agtcataagccatgaacat   149  (nucleotides 131-149 of SEQ ID NO:1)
               |||||||||||||||||||
Sbjct:   7185  agtcataagccatgaacat  7203

>gi|15451474|gb|AC009343.8| Drosophila melanogaster, chromosome 2R, region 47A-47B,
BAC clone BACR08L17, complete sequence
Length = 182494
 Score = 38.2 bits (19), Expect = 3.2
 Identities = 19/19 (100%)
 Strand = Plus/Minus Query:    167  cagcgaatacctaatgagc   185  (nucleotides 167-185 of SEQ ID NO:1)
               |||||||||||||||||||
Sbjct:  61278  cagcgaatacctaatgagc  61260

>gi|10727654|gb|AE003828.2|AE003828 Drosophila melanogaster genomic scaffold
142000013386047 section 15 of 52, complete sequence
Length = 259934
 Score = 38.2 bits (19), Expect 3.2
 Identities = 19/19 (100%)
 Strand = Plus/Minus Query:    167  cagcgaatacctaatgagc   185  (nucleotides 167-185 of SEQ ID NO:1)
               |||||||||||||||||||
Sbjct:  53026  cagcgaatacctaatgagc  53008

>gi|3900825|gb|AC005991.1|AC005991 Aspergillus parasiticus clone ap0, complete sequence
Length = 37754
 Score = 38.2 bits (19), Expect = 3.2
 Identities = 19/19 (100%)
 Strand = Plus/Minus Query:     22  aactgaggagaaaacgaga    40  (nucleotides 22-40 of SEQ ID NO:1)
               |||||||||||||||||||
Sbjct:  11194  aactgaggagaaaacgaga  11176
```

BlastX search

| Sequences producing significant alignments: | Score (bits) | E Value |
|---|---|---|
| gi|15234968|ref|NP_195630.1| (NC_003075) hypothetical prote | 32 | 1.8 |

Alignments

```
gi|15234968|ref|NP_195630.1| (NC_003075) hypothetical protein [Arabidopsis thaliana]
gi|7487352|pir||T08567 hypothetical protein T22F8.90 - Arabidopsis thaliana
gi|4914431|emb|CAB43634.1| (AL050351) hypothetical protein [Arabidopsis thaliana]
gi|7270902|emb|CAB80582.1| (AL161594) hypothetical protein [Arabidopsis thaliana]
   Length = 277
 Score = 31.6 bits (70), Expect = 1.8
 Identities = 19/60 (31%), Positives = 32/60 (52%), Gaps = 1/60 (1%)
 Frame = +2
Query:   23  TEEKTRQYVHETSVK*SEPEQSDAQS-NLNAENEP*MSHKP*TSHDQPHQRIPNEQMVSF 199 (SEQ ID NO:3)
             TE+KT++ + E  VK S+PE+   QS ++N E +  + HK  T        Q+ S+
Sbjct:  163  TEKKTKRIISEKKVKQSKPEKLTKQSTSVNREKQSEVEHKDITMTIEKQNLTEKRQIQSY 222 (SEQ ID NO:9)
```

The invention claimed is:

1. A method of producing a genetically engineered transgenic non-human organism comprising:
   (a) incorporating into a non-human organism a functional DNA sequence that confers a trait on said organism; and
   (b) incorporating into said organism a non-functional DNA sequence,
   wherein said non-functional DNA has no function in the organism other than that of providing information about said functional DNA, further wherein
      (i) said non-functional DNA sequence encodes an information message using a predefined coding scheme; and
      (ii) said information message provides information about said functional DNA sequence, and
   wherein said functional DNA sequence of (a) above and said non-functional DNA sequence of (b) above are incorporated into the same chromosome of said organism, thereby producing a genetically engineered transgenic non-human organism.

2. The method according to claim 1, wherein said functional DNA sequence is incorporated into said organism prior to said non-functional DNA sequence.

3. The method according to claim 1, wherein said non-functional DNA sequence is incorporated into said organism prior to said functional DNA sequence.

4. The method according to claim 1, wherein said non-functional DNA sequence and said functional DNA sequence are incorporated into said organism simultaneously.

5. The method according to claim 1, wherein said non-functional DNA sequence and said functional DNA sequence are located sufficiently close on said chromosome to prevent separation by recombination.

6. The method according to claim 1, wherein said non-functional DNA sequence is an intron or encodes an intein.

7. The method according to claim 6, wherein the intron or intein-encoding sequence is placed within the related functional DNA sequence.

8. The method according to claim 7, wherein the intron or intein-encoding sequence is placed within a conserved portion of the related functional DNA sequence.

9. The method according to claim 1, wherein said non-functional DNA sequence, optionally in conjunction with a spacer DNA sequence between said non-functional DNA sequence and said functional DNA sequence, is chosen such that it is not able to form secondary structures and/or such that it is free of recombination or mutation hot spots.

10. The method according to claim 1, wherein said mapping is from DNA portions to alphanumeric characters.

11. The method according to claim 1, wherein said predefined coding scheme translates DNA triplets to alphanumeric characters.

12. The method according to claim 1, wherein said non-functional DNA sequence comprises at least one pre-defined recognition sequence that allows for identification and/or analysis of said non-functional DNA sequence.

13. The method according to claim 12, wherein said non-functional DNA sequence is flanked at least on one side by the recognition sequence.

14. The method according to claim 12, wherein said pre defined recognition sequence comprises joint and/or separate recognition of multiple non-functional DNA sequences in the organism.

15. The method according to claim 12, wherein said pre defined recognition sequences are placed such to allow PCR amplification of said functional DNA sequence or portions thereof using primers complementary to said pre-defined recognition sequences.

16. The method according to claim 12, wherein said pre defined recognition sequence comprises joint and/or separate recognition of multiple non-functional DNA sequences in the organism.

17. The method according to claim 1, wherein the functional DNA sequence is flanked on both sides by portions of said non-functional DNA sequence.

18. The method according to claim 1, wherein said non-functional DNA sequence contains an additional DNA sequence encoding an expressible polypeptide for quick detection.

19. The method according to claim 1, wherein the information message comprises a trademark, a reference to a database, a date, a place, the name of a producer or an owner, or an indication of the presence and/or position of said functional DNA sequence, or any combination thereof.

20. The method according to claim 1, wherein said non-functional DNA sequence does not adversely affect the performance of said functional DNA sequence in said genetically engineered organism.

21. The method according to claim 1, wherein said incorporation into said organism of said non-functional DNA sequence does not adversely affect the genetic stability of said non-functional and/or said functional DNA sequence and/or the incorporation of said non-functional and said functional DNA sequence into the same chromosome of said organism.

22. The method according to claim 1, wherein the organism is a plant.

23. The method according to claim 1, wherein the organism is an animal.

24. The method according to claim 1, wherein said predefined coding scheme can be used to map a plurality of information messages to a plurality of said non-functional DNA sequences.

25. The method according to claim 1, wherein using said predefined coding scheme, said information message can be non-uniquely mapped to multiple non-functional DNA sequences and said nonfunctional DNA sequence can be uniquely mapped to said information message.

* * * * *

UNITED STATES PATENT AND TRADEMARK OFFICE
CERTIFICATE OF CORRECTION

PATENT NO.         : 7,667,091 B2
APPLICATION NO. : 10/471960
DATED                 : February 23, 2010
INVENTOR(S)      : Gleba et al.

It is certified that error appears in the above-identified patent and that said Letters Patent is hereby corrected as shown below:

Title Page 2, Other Publications:

Right Column, Line 17, "Boynton et al": Please correct "1688" to read --1988--

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

PATENT NO.      : 7,667,091 B2
APPLICATION NO. : 10/471960
DATED           : February 23, 2010
INVENTOR(S)     : Gleba et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 916 days.

Signed and Sealed this

Seventh Day of December, 2010

David J. Kappos
*Director of the United States Patent and Trademark Office*

SEQUENCE LISTING

<160> NUMBER OF SEQ ID NOS: 9

<210> SEQ ID NO 1
<211> LENGTH: 26
<212> TYPE: DNA
<213> ORGANISM: Artificial sequence
<220> FEATURE:
<223> OTHER INFORMATION: Synthetic PCR primer

<400> SEQUENCE: 1
gtcgactgaa tataatgcgc aaactg                                                26

<210> SEQ ID NO 2
<211> LENGTH: 29
<212> TYPE: DNA
<213> ORGANISM: Artificial sequence
<220> FEATURE:
<223> OTHER INFORMATION: Synthetic PCR primer

<400> SEQUENCE: 2
gaattctaaa tctgatgtgc aaattaagg                                             29

<210> SEQ ID NO 3
<211> LENGTH: 231
<212> TYPE: DNA
<213> ORGANISM: Artificial sequence
<220> FEATURE:
<223> OTHER INFORMATION: PCR amplification product
<220> FEATURE:
<221> NAME/KEY: CDS
<222> LOCATION: (23)..(199)

<400> SEQUENCE: 3

```
gtcgactgaa tataatgcgc aa act gag gag aaa acg aga caa tat gtt cat      52
                        Thr Glu Glu Lys Thr Arg Gln Tyr Val His
                         1               5                  10 gaa acg agt gtt aag tag agc gag cct gaa cag agc gac gcg cag agt      100
Glu Thr Ser Val Lys     Ser Glu Pro Glu Gln Ser Asp Ala Gln Ser
             15                  20                  25 aat ttg aac gcc gag aat gag cca tga atg agt cat aag cca tga aca      148
Asn Leu Asn Ala Glu Asn Glu Pro     Met Ser His Lys Pro     Thr
                 30                      35 tcg cat gac cag cct cat cag cga ata cct aat gag cag atg gtt tca      196
Ser His Asp Gln Pro His Gln Arg Ile Pro Asn Glu Gln Met Val Ser
 40                  45                  50                  55 ttc tcgccttaat ttgcacatca gatttagaat tc                              231
Phe
```

<210> SEQ ID NO 4
<211> LENGTH: 15
<212> TYPE: PRT
<213> ORGANISM: Artificial sequence
<220> FEATURE:
<223> OTHER INFORMATION: Synthetic Construct

<400> SEQUENCE: 4

Thr Glu Glu Lys Thr Arg Gln Tyr Val His Glu Thr Ser Val Lys
 1               5                  10                  15

<210> SEQ ID NO 5
<211> LENGTH: 18
<212> TYPE: PRT
<213> ORGANISM: Artificial sequence
<220> FEATURE:

-continued

<223> OTHER INFORMATION: Synthetic Construct

<400> SEQUENCE: 5

Ser Glu Pro Glu Gln Ser Asp Ala Gln Ser Asn Leu Asn Ala Glu Asn
1               5                   10                  15

Glu Pro

<210> SEQ ID NO 6
<211> LENGTH: 5
<212> TYPE: PRT
<213> ORGANISM: Artificial sequence
<220> FEATURE:
<223> OTHER INFORMATION: Synthetic Construct

<400> SEQUENCE: 6

Met Ser His Lys Pro
1               5

<210> SEQ ID NO 7
<211> LENGTH: 18
<212> TYPE: PRT
<213> ORGANISM: Artificial sequence
<220> FEATURE:
<223> OTHER INFORMATION: Synthetic Construct

<400> SEQUENCE: 7

Thr Ser His Asp Gln Pro His Gln Arg Ile Pro Asn Glu Gln Met Val
1               5                   10                  15

Ser Phe

<210> SEQ ID NO 8
<211> LENGTH: 60
<212> TYPE: PRT
<213> ORGANISM: Arabidopsis thaliana

<400> SEQUENCE: 8

Thr Glu Lys Lys Thr Lys Arg Ile Ile Ser Glu Lys Lys Val Lys Gln
1               5                   10                  15

Ser Lys Pro Glu Lys Leu Thr Lys Gln Ser Thr Ser Val Asn Arg Glu
            20                  25                  30

Lys Gln Ser Glu Val Glu His Lys Asp Ile Thr Met Thr Ile Glu Lys
        35                  40                  45

Gln Asn Leu Thr Glu Lys Arg Gln Ile Gln Ser Tyr
    50                  55                  60

<210> SEQ ID NO 9
<211> LENGTH: 60
<212> TYPE: PRT
<213> ORGANISM: Arabidopsis thaliana

<400> SEQUENCE: 9

Thr Glu Lys Lys Thr Lys Arg Ile Ile Ser Glu Lys Lys Val Lys Gln
1               5                   10                  15

Ser Lys Pro Glu Lys Leu Thr Lys Gln Ser Thr Ser Val Asn Arg Glu
            20                  25                  30

Lys Gln Ser Glu Val Glu His Lys Asp Ile Thr Met Thr Ile Glu Lys
        35                  40                  45

Gln Asn Leu Thr Glu Lys Arg Gln Ile Gln Ser Tyr
    50                  55                  60